US005824886A

United States Patent [19]
Selby et al.

[11] Patent Number: 5,824,886
[45] Date of Patent: Oct. 20, 1998

[54] FOAM TESTER

[75] Inventors: Theodore W. Selby, Midland; Michael A. Tubbs, Holland; Joseph S. Trombley, Auburn; James R. Cotter, Bay City; Gregory C. Miiller, Coleman, all of Mich.

[73] Assignee: Tannas Co., Midland, Mich.

[21] Appl. No.: 782,822

[22] Filed: Jan. 13, 1997

Related U.S. Application Data

[60] Provisional application No. 60/012,576 Feb. 29, 1996, and 60/026,429, Sep. 20, 1996.

[51] Int. Cl.$^6$ .............................. G01N 37/00; H05B 3/06
[52] U.S. Cl. ........................ 73/60.11; 219/523; 219/531
[58] Field of Search .............................. 73/53.01, 53.05, 73/60.11, 61.46, 866; 219/521, 522, 523, 530, 531, 535; 422/89, 99, 102, 104

[56] References Cited

U.S. PATENT DOCUMENTS

| | | | |
|---|---|---|---|
| 785,524 | 3/1905 | Shea | 422/102 |
| 1,673,333 | 6/1928 | Klumpp | 219/521 |
| 1,694,725 | 4/1928 | Tabb | 219/521 |
| 1,763,461 | 6/1930 | Fowler | 422/104 |
| 1,829,600 | 10/1931 | McGregor | 219/521 |
| 2,299,401 | 10/1942 | Melton | 219/19 |
| 2,380,679 | 7/1945 | Smith | 73/60.11 |
| 2,418,254 | 4/1947 | Fleharty | 219/521 |
| 2,907,861 | 10/1959 | Melton | 219/521 |
| 3,027,755 | 4/1962 | Groll et al. | 73/60.11 |
| 3,028,473 | 4/1962 | Dyer et al. | 219/521 |
| 3,779,731 | 12/1973 | Pollock et al. | 65/29 |
| 3,971,630 | 7/1976 | Sandrock et al. | 23/230 R |
| 4,356,967 | 11/1982 | Lunick | 237/14 |
| 4,572,427 | 2/1986 | Seleridge et al. | 236/3 |
| 4,577,491 | 3/1986 | Callaghan et al. | 73/60.11 |
| 4,678,752 | 7/1987 | Thorne et al. | 435/291 |
| 5,073,697 | 12/1991 | Uchiyama | 219/385 |
| 5,154,088 | 10/1992 | Lehnert et al. | 73/866 |
| 5,271,085 | 12/1993 | Carballo | 392/444 |
| 5,336,866 | 8/1994 | Winstead et al. | 219/411 |
| 5,456,147 | 10/1995 | Strange, Jr. | 83/74 |
| 5,460,441 | 10/1995 | Hastings et al. | 312/298 |
| 5,465,610 | 11/1995 | Loisel | 73/60.11 |
| 5,501,839 | 3/1996 | Tarantino | 422/99 |
| 5,549,473 | 8/1996 | Valentian | 432/239 |
| 5,597,950 | 1/1997 | Mullen | 73/60.11 |
| 5,661,978 | 9/1997 | Holmes et al. | 62/3.2 |

FOREIGN PATENT DOCUMENTS

| | | |
|---|---|---|
| 252738 | 1/1988 | European Pat. Off. . |
| 1186105 | 4/1970 | United Kingdom . |
| 1313970 | 4/1973 | United Kingdom . |
| 2157833 | 10/1985 | United Kingdom . |
| 2169086 | 7/1986 | United Kingdom . |

OTHER PUBLICATIONS

ASTM Designation D 892–92, Standard Test Method for Foaming Characteristics of Lubricating Oils, 1992.
Lubrication Technology, Savant, Inc., "Foam Testing Now Available," Sep. 1996, pp. 1 & 4.
P 102, 1974, Arthur H. Thomas Co. Parts Catalog.

Primary Examiner—Michael Brock
Assistant Examiner—Jay L. Politzer
Attorney, Agent, or Firm—Christopher John Rudy

[57] ABSTRACT

Foam tester device, which is useful for testing the foaming of liquids at elevated temperatures, has an insulated cabinet containing a temperature-regulatable volume; a heater capable of heating a gas for the volume; a feature to circulate heated gas in the volume; an access system such that sample container(s), each capable of holding a liquid sample, is(are) insertable into the volume so as to be heated; and a feature, for example, a window, to observe any sample(s) in the sample container(s) such that observation can be conducted from outside the cabinet. The foam tester is a gas, especially air, bath. Cooling may be provided by water or other liquid, for example, propylene glycol and water mixture, and/or by insert of a cooling device, for example, a cooling carosel or insert drawer in place of the foam tester sample carousel. Foam test operation is simplified, and the foam tester may be employed to operate sample testing cycles without removal of samples from the tester between tests.

16 Claims, 8 Drawing Sheets

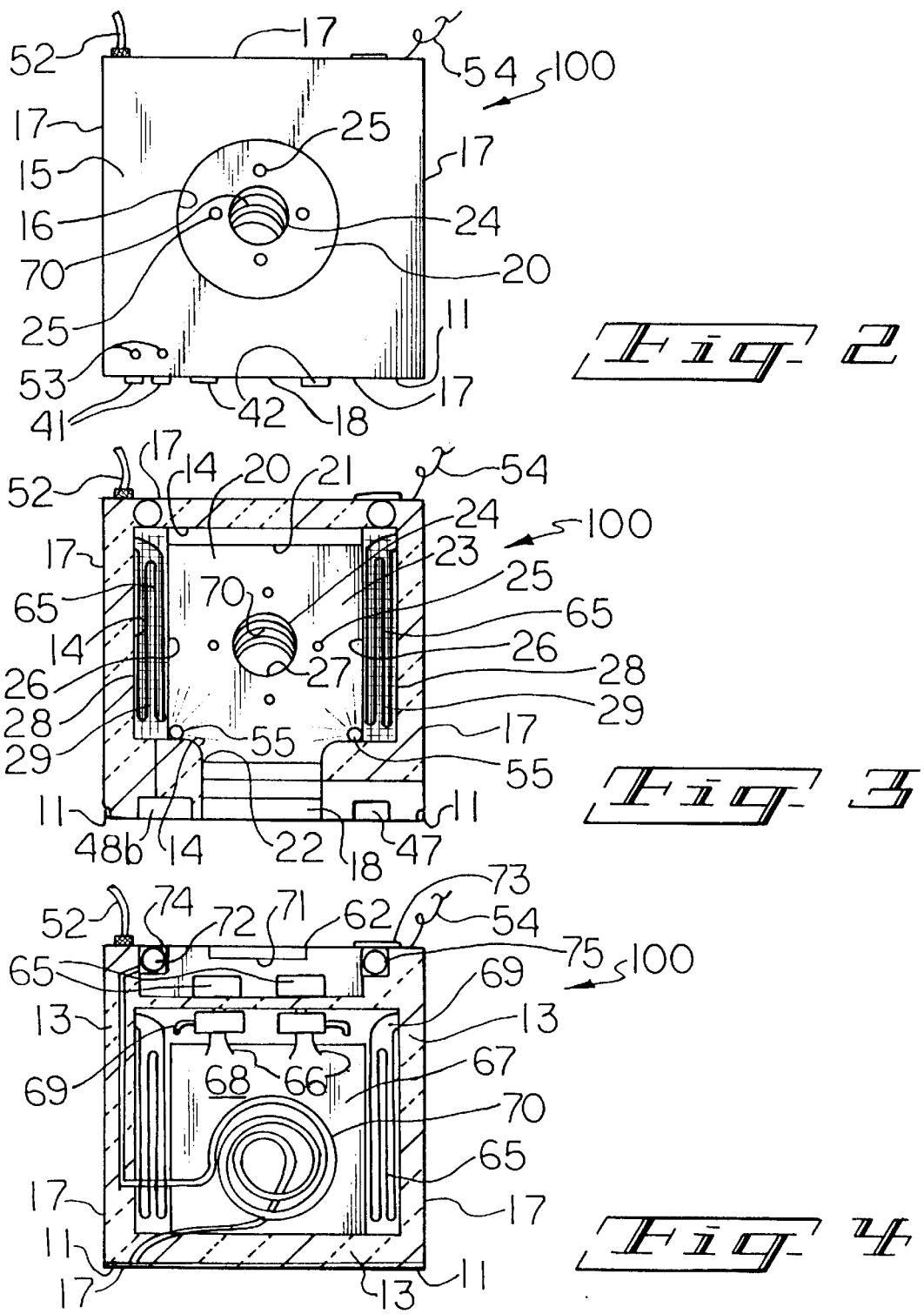

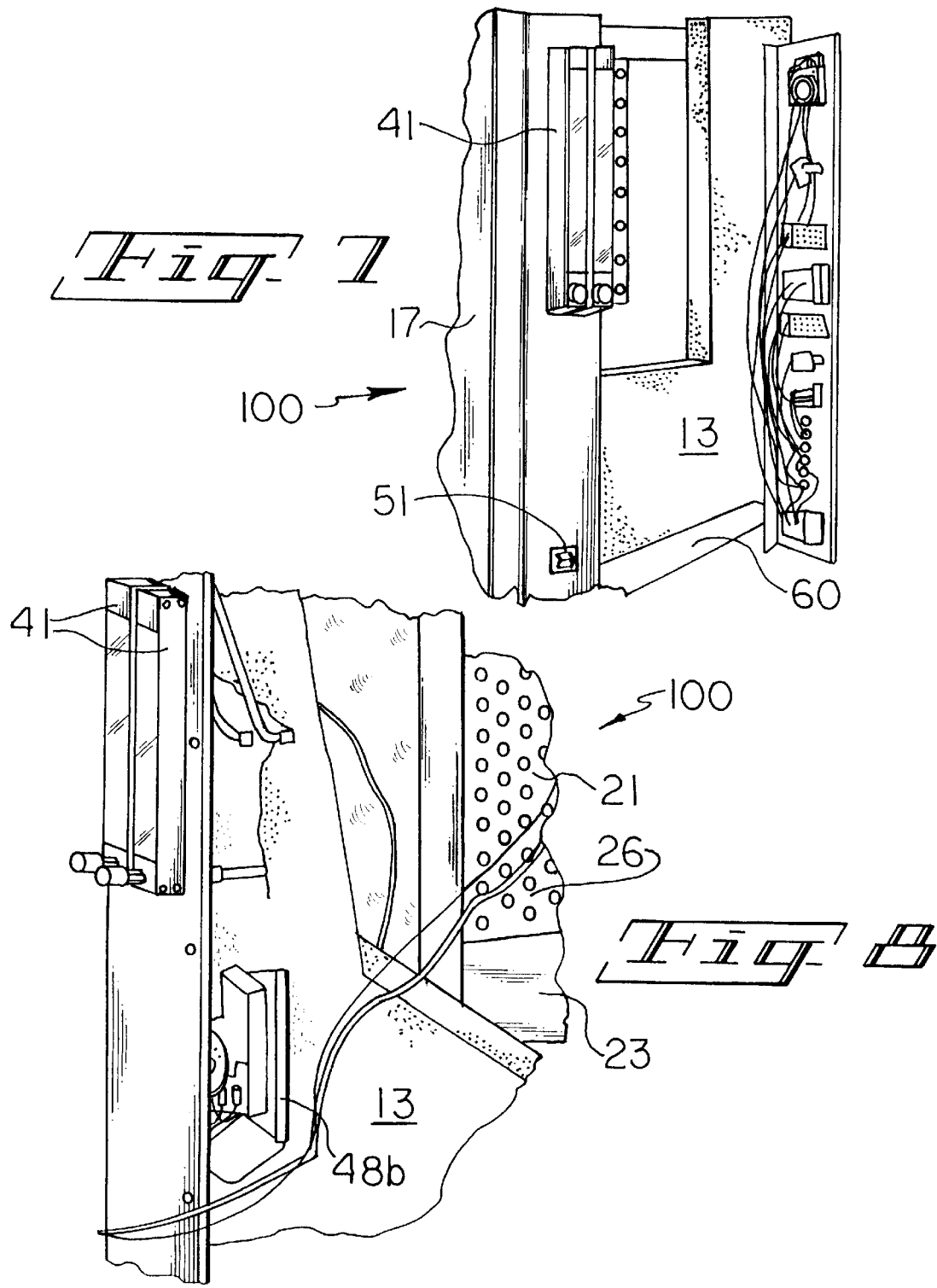

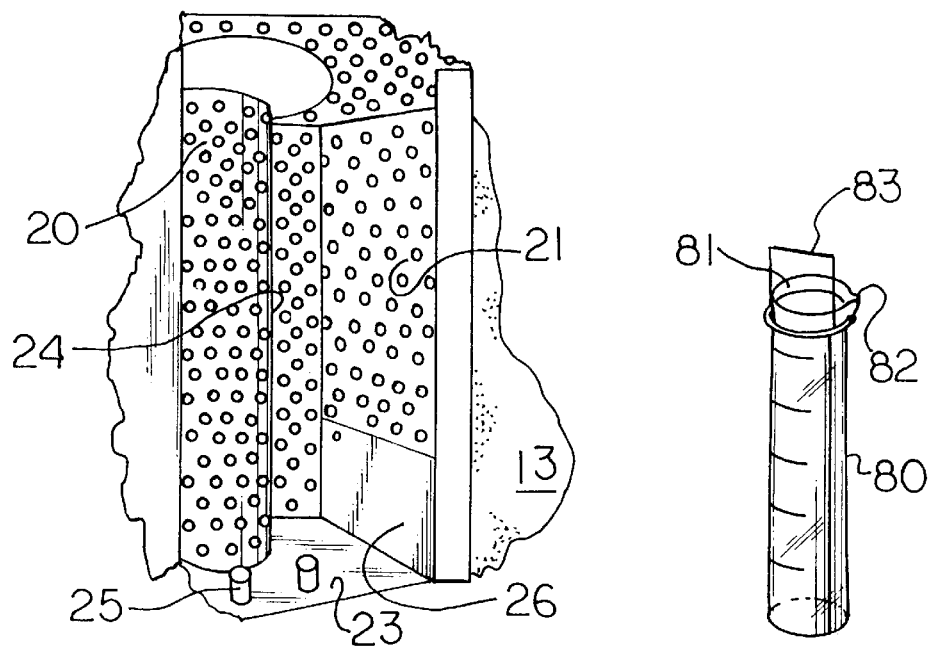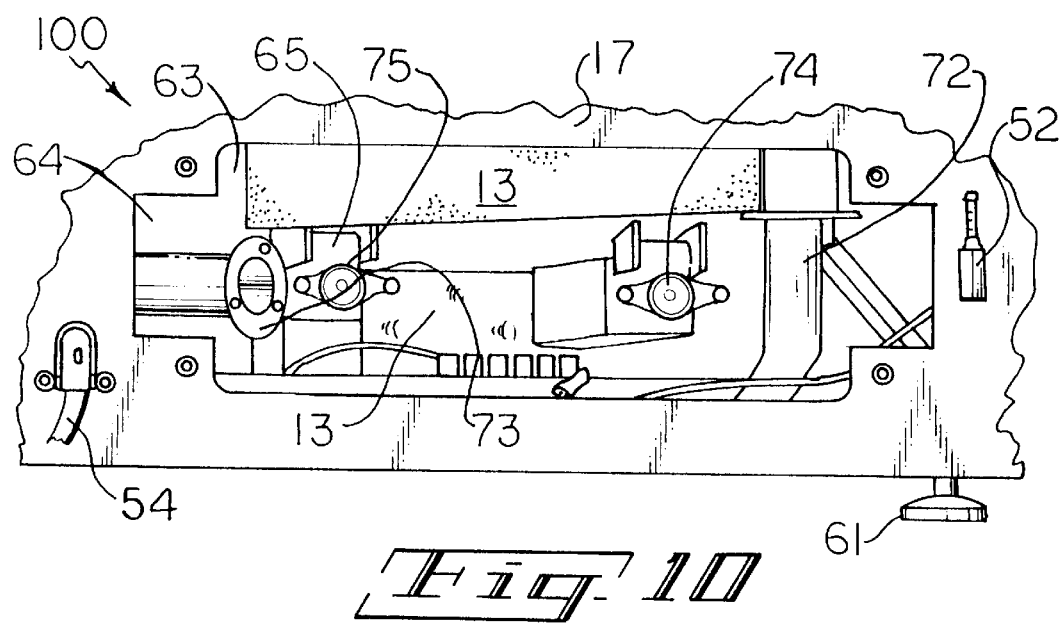

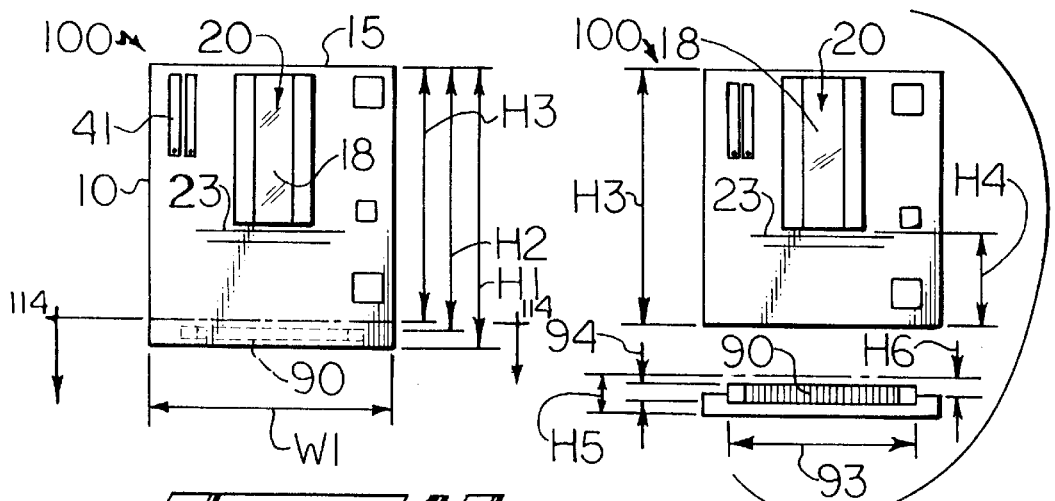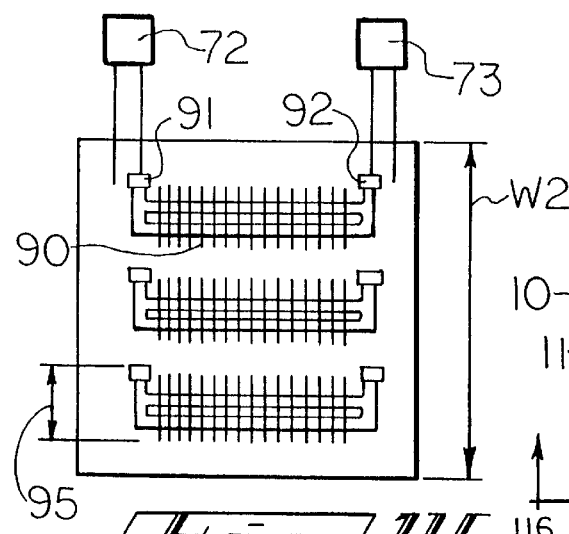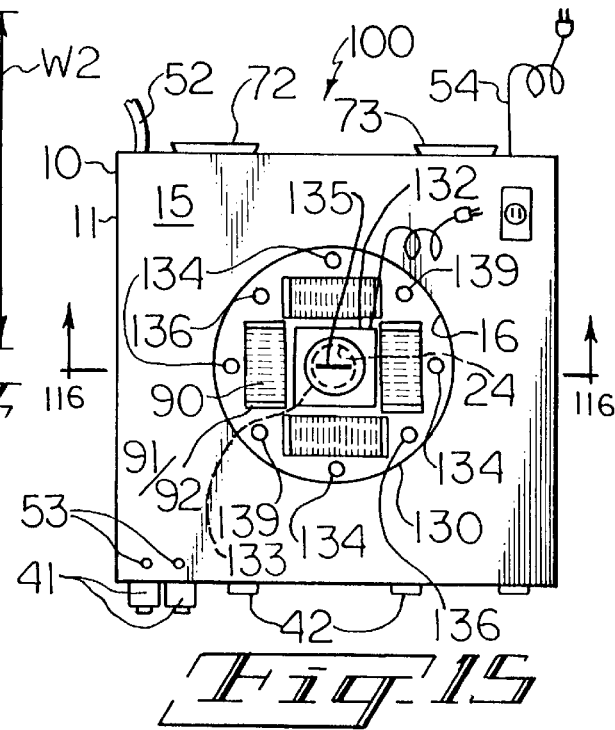

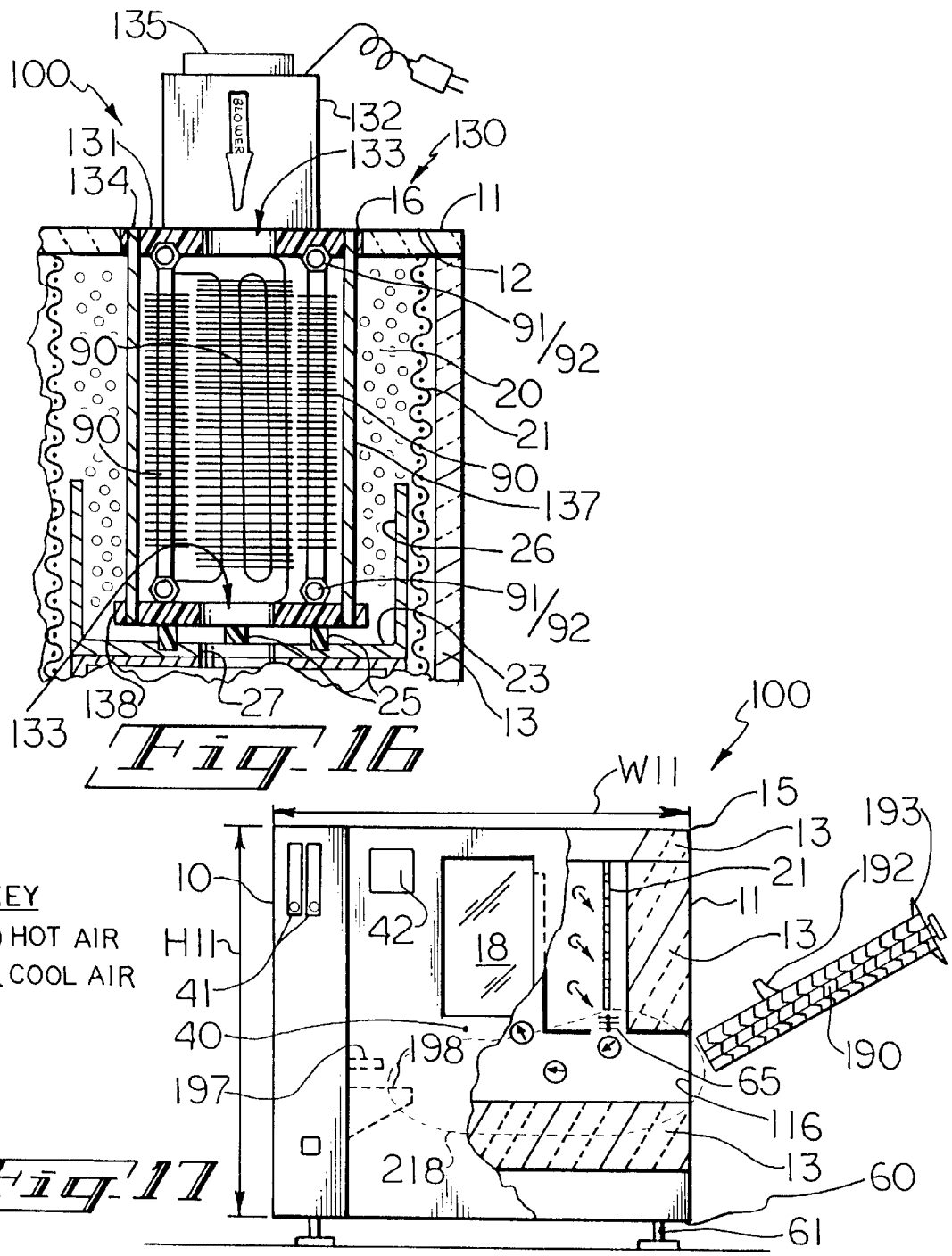

FOAM TESTER

This incorporates by reference provisional U.S. application Ser. Nos. 60/012,576 filed Feb. 29, 1996 & 60/026,429 filed Sep. 20, 1996. The benefit of the same is claimed herein.

FIELD

This invention concerns a foam testing device, useful for testing the foaming of liquids at elevated temperatures.

BACKGROUND

One of the problems with liquids including lubricants is the foam which can form under operating conditions. In order to test this, and in the process determine a standard property of such liquids, techniques such as the ASTM D 892 test method have been used for some time.

In the ASTM D 892 test method, foaming characteristics of lubricating oils are determined at temperatures up to 93.5 degrees Celsius. An air bubbling stone is set in the sample; the sample is heated appropriately as air is bubbled in, and foam characteristics of the sample are observed over a period of time.

However, with the advent of modern engines, the oils and other lubricants which are employed in the engines are made subject to higher and higher operating temperatures. Thus, it becomes desirable to test for the characteristics of such fluids at or above such temperatures, and among such desired tests is a high temperature foaming test, up to and above 150 degrees C.

However that may be, currently available liquid-filled baths to test for and monitor foam characteristics, and in particular as might be encountered at high temperatures, have several drawbacks. Among these drawbacks are included the following:
1) A lack of an ability to heat and cool quickly.
2) A lack of ability to see through the bath liquid.
3) Requirement of more than one bath.
4) Requirement of frequent bath liquid changes.
5) Difficulty of handling sample containers coming from the liquid bath and coated with hot oil.
6) Difficulty of operation.

Accordingly, it would be desirable to improve upon such.

SUMMARY

The present invention provides a foam tester comprising an insulated cabinet with a temperature-regulatable volume contained therein; a heater capable of heating a gas for the volume; a feature to circulate heated gas in the volume; an access system such that sample container(s), each capable of holding a liquid sample, is(are) insertable into the volume so that the same can be heated therein; and a feature to observe any sample(s) in the sample container(s) such that observation can be conducted from outside the cabinet. The foam tester of the invention is a gas, especially air, bath. Provided in further embodiments of the foam tester device is the improvement where cooling is provided by water or other liquid and/or by insert of a cooling device, for example, an insert in place of a foam tester sample carousel.

The invention is useful in testing liquids for foaming at elevated temperatures.

Significantly, by the invention, a major step forward is made in the art of foam testing of liquids. Many if not all of the aforementioned problems in the art are addressed, and the much if not all of the same ameliorated or overcome. By its air bath—sample visibility, sample container removal, and safety are enhanced. Operation is simplified, and the foam tester may be employed to operate sample testing cycles without removal of samples from the tester between tests. Nonetheless, in addition or as a nice alternative, cooling of the foam tester can be most efficiently provided by the liquid and/or insert cooling device.

Numerous further advantages attend the invention.

DRAWINGS

The drawings form part of the specification hereof. In the drawings, which are not necessarily drawn to scale and in which like numerals generally refer to like features, the following is briefly noted:

FIG. 2 is a top view of the foam tester of FIG. 1.

FIG. 3 is a top, cut-away view of the foam tester of FIG. 1, taken along 3—3.

FIG. 4 is a top, cut-away view of the foam tester of FIG. 1, taken along 4—4.

FIG. 7 is a front perspective view of part of the foam tester as of FIG. 5, looking from left to right and viewing the back of the right hand side instrument panel and wiring.

FIG. 8 is a front perspective view of part of the foam tester as of FIG. 5, but at an earlier stage of manufacture, looking from right to left.

FIG. 9 is a front perspective view of part of the foam tester as of FIG. 5, focusing in upon its sample oven.

FIG. 10 is a rear perspective view of part of the foam tester as of FIG. 5, with its lower back access panel and motor cooling fan removed.

FIG. 11 is a perspective view of a sample container of the invention.

FIG. 12 is front view of a further embodiment of a foam tester of the invention, having water cooling.

FIG. 13 is an exploded view of the foam tester of FIG. 12.

FIG. 14 is a sectional view of the foam tester of FIG. 12, taken along 114—114.

FIG. 15 is a top view of a further embodiment of a foam tester of the invention, having cooling by a carousel insert.

FIG. 16 is a sectional view of the foam tester of FIG. 15, taken along 116—116.

FIG. 17 is a front, partial cut-away, plan view of a further embodiment of a foam tester of the invention, having cooling by a cooling drawer insert.

ILLUSTRATIVE DETAIL

Figure 1:
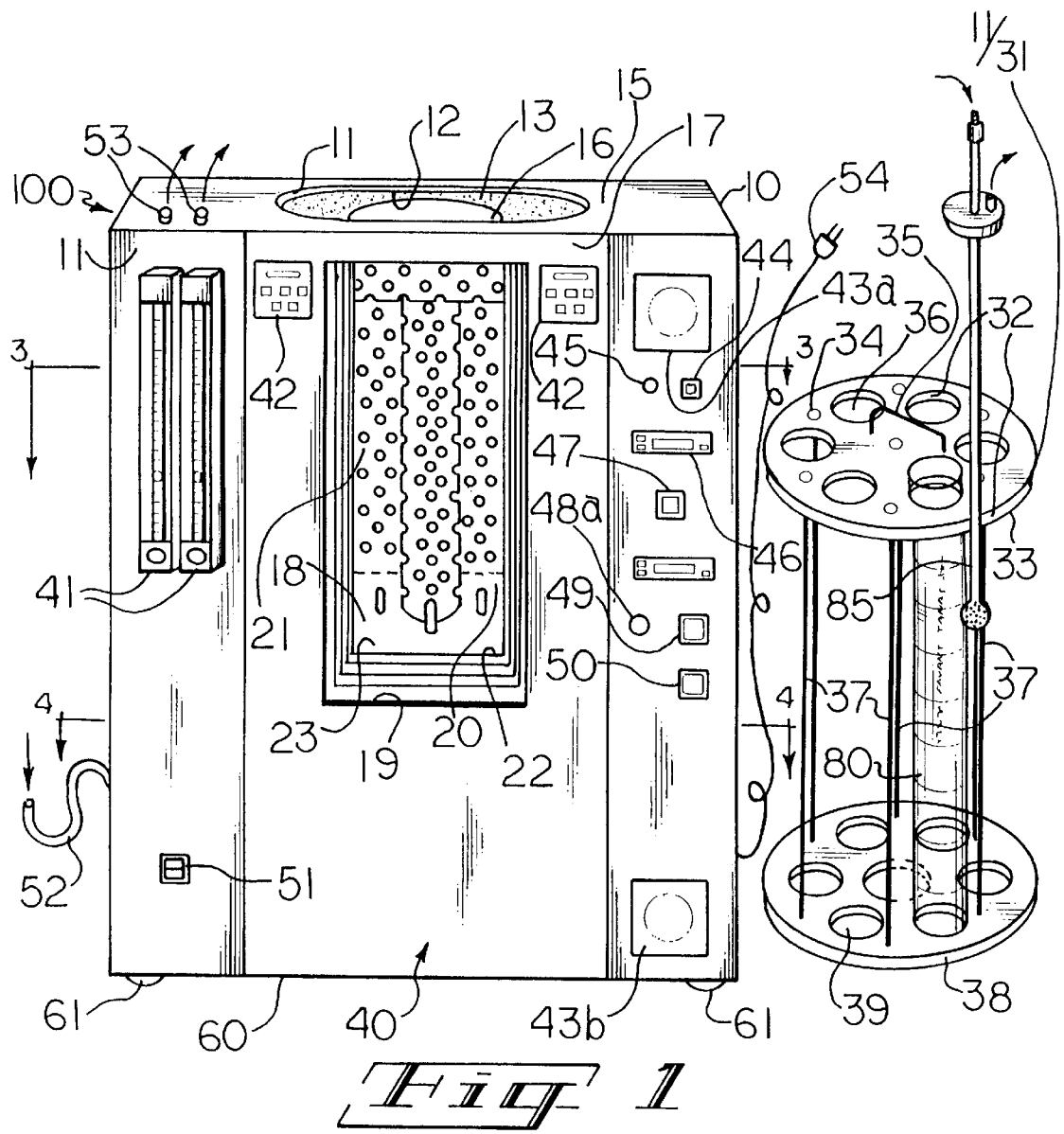
FIG. 1 is a front view of a foam tester of the invention with its carousel removed and shown alongside the cabinet.
Figure 5:
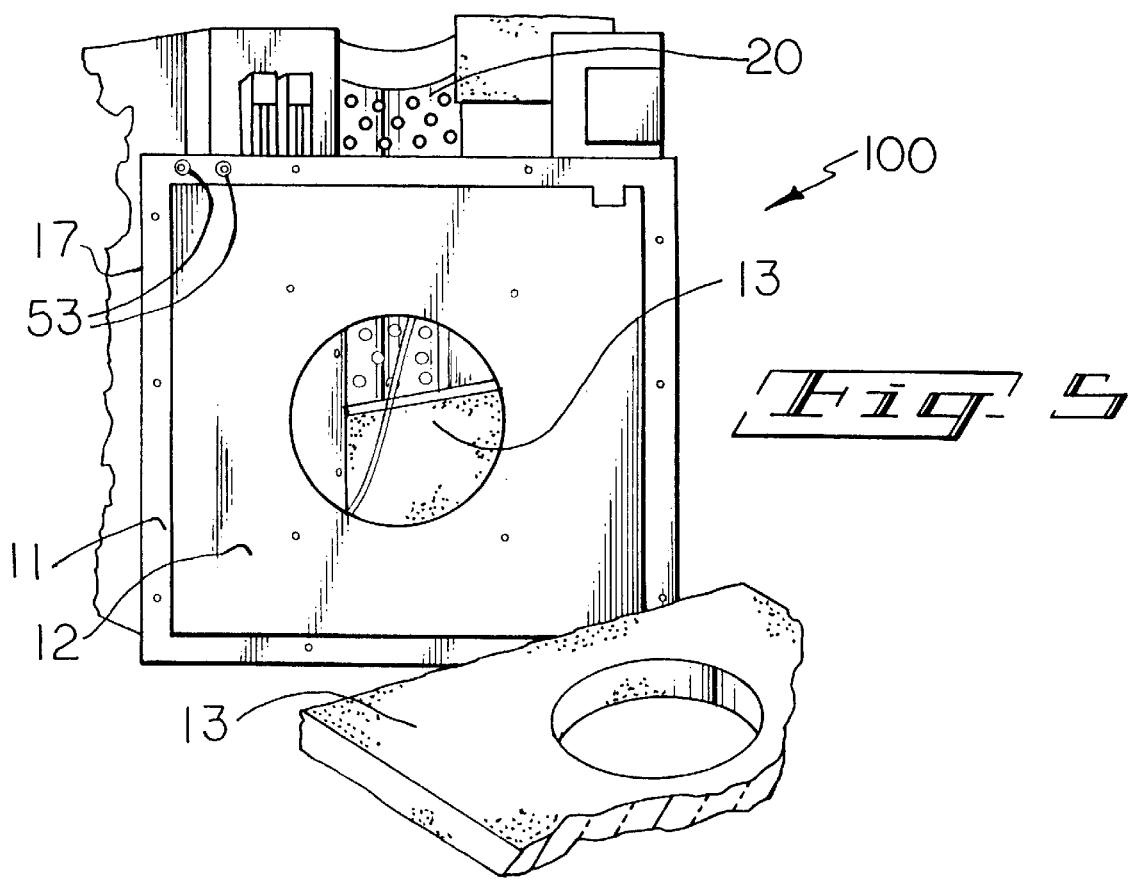
FIG. 5 is a view from the front of the foam tester of FIGS. 1–4, partially disassembled with its front window removed and its top and top insulation in the foreground.
Figure 6:
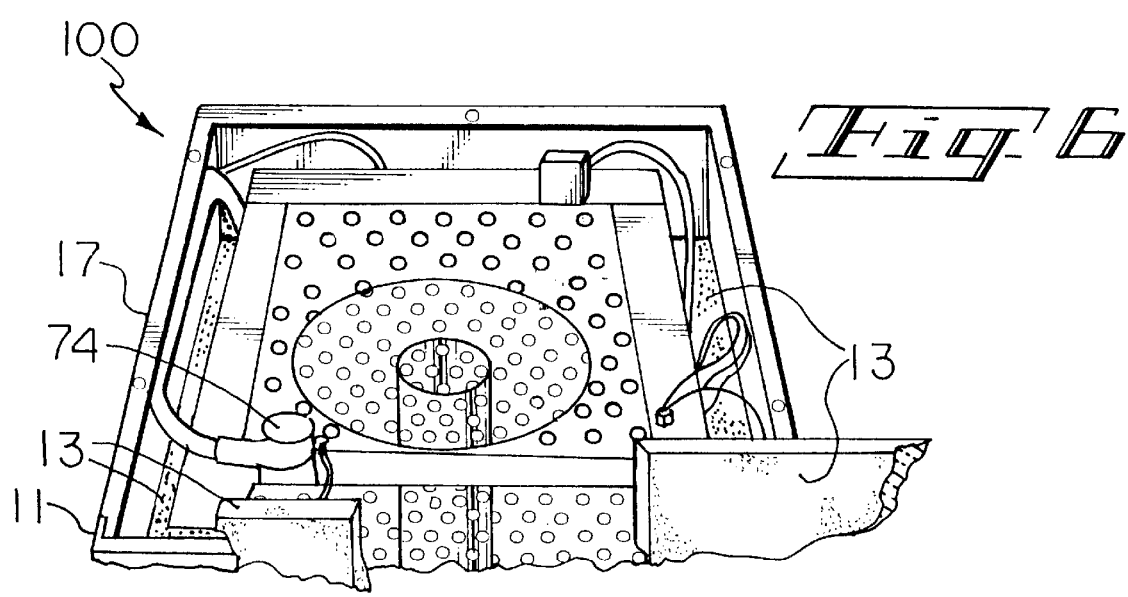
FIG. 6 is a top perspective view of part of the foam tester as of FIG. 5.

The invention can be further understood by reference to the present detail, taken in conjunction with the drawings. The same is to be construed in an illustrative and not necessarily limiting sense.

In FIGS. 1–10 is depicted foam tester 100.

The foam tester 100 has an insulated cabinet including a housing 10 with suitable outside dimensions, for example, about twenty-one by twenty-one inches and about twenty-five inches high. The tester 100 can have multi-surfaced outside such as including outside plastic layers 11 of ¼-inch thick KYDEX thermoplastic on top and in front corner panels. Top subsurface 12 can be a high-temperature-withstanding plastic such as a ¼-inch thick phenolic material which can withstand use in temperatures up to about three hundred and fifty degrees Fahrenheit. Insulation 13 is any suitable, which includes, for example, a high-temperature-withstanding glass or mineral fiber material some two inches or so thick which can withstand use in temperatures up to about one thousand degrees Fahrenheit. Inside wall 14, for example, of about ³⁄₆₄-inch to ¹⁄₁₆-inch or so metal such as aluminum or steel to include stainless steel, for example, aluminum, butts up to the insulation 13. Top 15 has access opening 16 therein, for example, a circle about ten inches in diameter. The cabinet multi-surfaced outside can also include an about ³⁄₆₄-inch to ¹⁄₁₆-inch or so metal sheet layer 17 such as of aluminum or steel, for example, of stainless steel. Window 18 is present, which preferably is a multi-paned structure with a see-through gas between the panes, or with reduced pressure gas or a vacuum between panes; for example, there may be four panes of tempered safety glass, with the outermost (forming a boundary with the outside environment) and innermost (forming a boundary with the tester interior) being some ¼-inch in thickness, and the two panes between the outermost and innermost panes being some ⅛-inch in thickness, each with about atmospheric pressure air serving as the see-through gas between panes. Materials other than glass may be employed in a pane, for example, polycarbonate plastics, and so forth. The window 18 may be any suitable size, for example, six or so inches wide by fifteen inches high. An outside window gasket 19 can form a seal with the window 18 and outside panel 17 proximate the window. Parts such as panels, and so forth, may be assembled with suitable fasteners, which can include screws, and so forth.

A temperature-regulatable volume, which may be termed an oven volume 20, is contained in the insulated cabinet of the foam tester 100. Within the volume 20 is a circulating cage, which may be termed an air diffuser, defined in part by cage wall 21, which can be of any suitable perforate material including glass or mineral fiber sheets, metal sheets and/or screens such as of aluminum or steel including stainless steel, and so forth. For example, a ³⁄₆₄-inch to ¹⁄₁₆-inch or so thick aluminum sheet patterned with ⅜-inch to ½-inch diameter holes spaced suitably close to one another can be employed to good effect as the cage wall 21. Inside window pane gasket 22, for example, of woven glass or mineral fiber belt construction, can provide a seal between the window 18 and oven volume 20 wall structure, which is generally imperforate about the front or window side. Oven floor 23, for example, about twelve inches wide by twelve to thirteen or fourteen inches in depth from window 18 to the rear of the oven volume 20, provides a lower boundary to the oven volume 20, and it may be of any suitable material, for example, of suitably thick sheet aluminum. A circulation stack 24 is mounted approximately central in a hole in the oven floor 23 and provides access to a lower, venturi chamber. The stack 24, which may be termed an air plume, is made of a suitable perforate material such as glass or mineral fiber, or metal including aluminum or steel, for example, being cylindrical and about fifteen inches high by three inches in diameter of ³⁄₆₄-inch to ¹⁄₁₆-inch thick stainless steel with a hole pattern such as found in the cage wall 21. A number of carousel support posts 25, for example, three or four in number, rise from the bottom of the oven floor 23. The posts 25, as depicted, may be simple, heat-resistant plastic standoffs. Alternatively, they may have leveling machine capability such as may be afforded by a bolt and nut arrangement, and so forth. Lower, imperforate side heater protection panels 26, which may be of any suitable material such as aluminum or steel including stainless steel, may rise up several inches, for example, about four inches, from the oven floor 23 on the sides of the oven volume 20 up to perforate cage walls 21, the cage walls 21 further rising to a suitable height, for example, some fifteen inches above the oven floor 23. The side cage walls 21 and lower panels 26 are any suitable depth, for example, being some twelve inches in depth to connect with rear, perforate cage wall 21, which, for example, is some twelve inches wide by fifteen inches high. The cage walls 21 are spaced a suitable distance from the inside walls 14, for example, with cage walls 21 being some two inches from the inside walls 14 on each side and the cage wall 21 being about an inch or so from the inside wall 14 at the rear of the oven volume 20. Floor drain 27 may be provided by the hole in the oven floor about or in which is mounted stack 24, or a separate floor drain (not depicted) may be provided in the oven floor 23, for example, which can be directed through the housing 10 at the front so as to collect and monitor any spills which may occur such as by breaking of a glass sample container in the oven volume 20. The volumes between the inside walls 14 (side) and the lower panels 26 provide side channels 28 for heating elements, each of which is covered by a top grate or screen 29 which is positioned four inches higher than the oven floor 23.

Carousel 30 is removably insertable into the oven volume through access opening 16 and rests on the carousel support posts 25. It has outside layer 31 of any suitable material, for example, of ¼-inch thick material the same as the outside layer 11, insulative core 32, for example, of a ⅝-inch thick heat-resistant foam, and internal layer 33, for example, of relatively thin hard, heat-resistant plastic laminate, all of which can be connected in suitable fashion including by suitable glue; mechanical fasteners, for example, six nut and bolt fasteners 34; and so forth. Handle 35, for example, of stainless steel, is present to lift and move the carousel 30 with any cargo. A number of sample cylinder holes 36, for example, six 2⅝-inch diameter circular holes run through the layers 31 & 33, which holes have diameters of about 2½ inches through the rather flexible foam insulative core 32, to provide access for sample cylinders. A number of support rods 37, for example, six ⅜-inch TP304/304L ASTM A269 stainless steel rods, connect the aforementioned carousel top portion assembly to carousel base 38 some fifteen inches below the top portion assembly. The base 38 is of any suitable heat-resistant material, for example, of the hard, heat-resistant plastic laminate used with the layer 33 but about ¼-inch in thickness with a number, for example, six, sample cylinder cups 39, each of which is of a suitable dimension to accommodate a sample cylinder, for example, being circular with an about 2⁹⁄₁₆-inch diameter and ³⁄₁₆-inch depth.

Front panel area 40 can have flow gages 41 to include those which are calibrated and capable of maintaining an air or other gas flow volume of about two hundred milliliters (mL) per minute, for example, dual Gilmont Industries Model: 150MM—Part: GF-5531-2217 ball air flow gages, for controlling and monitoring the flow of air which goes for providing air for a bubbling stone to make foam during liquid testing; one or more digital timers 42, which may be mounted in such manners as glue and/or mechanical fasteners including clips, hook and loop fastening materials, screws, and so forth, with VELCRO hook and loop material advantageously employed so as to be able to readily change batteries on commercially obtained timers; and an instrument cooling system 43 with, for example, instrumentation temperature control fan 43a in an upper position which cycles air out, and instrumentation temperature control vent 43b in a lower position which permits cooler outside air to be drawn in, especially upon action of the fan 43a. The front panel area 40 can also include a main on/off switch 44; an instrument fuse 45, in position for ready replacement if necessary; a temperature readout system, for example, dual temperature readout displays 46; a high/low setting switch 47 for air temperature in the oven volume; a high-temperature cut-out system 48, which includes high-temperature cut-out indicator panel light 48a controlled by high-temperature cut-out control device 48b interior of the panel 40, which senses for too high a temperature over an oven heating element; automatic oven volume heater heating on/off switch 49; a fan switch 50 with on/automatic settings; and oven chamber 20 cooling fans on/off switch 51.

Also present with the tester 100 can be air inlet 52 for providing air or other gas for heating and flow monitoring to supply air of other gas for bubbling in a sample to make foam; air exit ports 53 from which can exit flow-monitored, warmed air for delivery to the sample bubbling stones for making of the foam; an electric power supply cord 54; and oven lights 55, which assist in providing illumination in the oven volume 20 so as to better observe the test sample.

Bottom 60 may be a suitably strong member or part of the housing, for example, being of $\frac{1}{8}$-inch thick steel. Legs 61 may be in four corners of the tester 100, and be adjustable so as to facilitate leveling. Lower back access panel 62, for example, of perforated stainless steel about $\frac{3}{64}$-inch to $\frac{1}{16}$-inch in thickness, can cover back access opening 63. Inside mounting plate 64 can be present and stand off above the bottom 60.

The tester 100 has a heater 65 capable of heating a gas, especially air, for the oven volume 20. The heater 65 may be in the form of dual electric resistance heaters, each of which is generally positioned behind one of the panels 26.

The tester 100 has a feature which may include a means to circulate heated gas in the volume, which generally include circulation motor(s) 66, for example, dual $\frac{1}{40}$-horsepower, 3000-rpm, i.e., rotations per minute, 115-volt, 60-Hz, 1.1-amp, TPL motors, each with a venturi opening to draw air from a negative pressure venturi chamber 67. The venturi chamber 67 can be any suitable size and material, for example, being an aluminum box about twelve by twelve inches by five inches high, which opens through its top to oven volume 20 through the air plume 24. The venturi chamber is insulated, for example, with about two inches of insulation 13 such as the aforementioned mineral fiber insulation surrounding its sides and bottom, and the bottom 68 of the venturi chamber on its outside stands off from the cabinet bottom 60 about two inches with four phenolic standoff sticks (not depicted) running parallel to one another, between which are stuffed insulation. Air or other gas within the foam tester 100 is pumped from the venturi chamber 67 through the circulation motors 66 and to a positive pressure plenum 69, for example, provided as dual positive pressure plenums on each side of the foam tester. From there, the air travels by and around the heater 65 to be heated so as to heat sample liquid(s) in sample cylinder(s) in the carousel 30 in place in the top 15 of the foam tester 100.

Accordingly, an access system is provided such that sample container(s), each capable of holding a liquid sample, is(are) insertable into the volume so that the same can be heated therein. Although the carousel 30 is a preferred embodiment of the access system, alternative access systems may be employed. For an example, sample containers can be inserted directly through holes in the top of the foam tester without there being a carousel or similar sample container holding device. Doors, whether sliding or swinging, drapes, and so forth may also be employed as or in conjunction with the access system.

The foam tester 100 has a feature to observe any sample (s) in the sample container(s) such that observation can be conducted from outside the cabinet. For example, the window 18 can be or be a part of a means to observe. Other means to observe may be employed such as periscope(s), optical fibers, mirror(s) or prism(s) in configurations other than in periscopefs), lens(es), video camera(s), digital camera(s), and so forth and the like.

Further features may be present in the foam tester 100.

For example, sample bubbling gas, especially including air, which makes for test foam, can be preheated or tempered by travel through bubbling gas tempering coil(s) 70 disposed in the venturi chamber 67, before being bubbled through sample, say, at forty-nine degrees Celsius. The tempered gas may be controlled and monitored by the gas or air flow gages 41 and exit the cabinet housing 10 through exit(s) 53.

Motor-cooling fan 71 can be positioned on the lower back perforate panel 62. The fan 71 can provide air circulation for oven operational motors 65, and auxiliary, oven volume cool-down motors 72 & 73.

For example, one oven cool-down motor 72 can be a blower type, which takes cooler air from the environment external to and blows it into the oven volume 20 of the foam tester 100, and the other 73 a sucking type, which draws hot air from the oven volume 20 and expels it into the external environment. To facilitate this, conduit 74 can lead from the blowing motor 72 to one corner of the upper portion of the oven volume 20 between the inside wall 14 and the circulation cage wall 21, and conduit 75 can lead from the sucking motor 73 to an opposite corner of the upper portion of the oven volume just inside the circulation cage wall 21. For example, the motors 72 & 73 generally may be of a $\frac{1}{500}$-horsepower, 115-volt, 60-Hz, 0.35-amp, 3300-rpm continuous duty impedance protected type or the like. The interior gas or air volume of the foam tester 100 may be swept clean some three or more times a minute accordingly, and higher sweeping capacities for quicker cool-down cycles can be engendered by greater capacity motor(s).

In FIGS. 1 & 11 can be seen sample cylinder 80, which can have lip 81 with pour spout 82, which may be V-shaped or the like, above the cylinder wall portion thereof. The spout 82 does not enter into the cylinder wall, and thus, no interference with sealing as, for example, with a rubber stopper element of a bubbling wand assembly, for testing. The cylinder 80 can be a 1000-mL graduated cylinder which is about 15½ inches high and about 2½ inches in external diameter. Bail 83 may serve as a handle. Alternatively, conventional sample cylinder(s) may be employed. Air or other gas, preferably tempered or pre-warmed, can enter the sealingly engaged bubbling wand assembly 85, shown outside the cylinder 80 in FIG. 1, when inserted into the cylinder 80 containing test liquid so as to create fine bubbles of the air or other gas in the test liquid to cause the foaming which is monitored by observation in standard or other more locally utilized testing procedures. A foam generating gas such as air, for example, can be routed into and out of pertinent entrance and exit hole(s) or coupling(s) of the foam tester 100 with bubbling wand assembly 85 as indicated by the arrows which may be seen in FIG. 1. Thus, suitable conduit(s) are employed to route the air from air exit(s) 53 to the bubbling wand assembly(ies) 85.

Advantageously, the testing procedure is carried out at an elevated temperature, for example, at temperatures up to 93½ or one hundred fifty degrees Celsius, or even higher. In test procedures which require that the test liquids be subject to heating and cooling cycles such as with a sample preheating phase, for example, to about forty-nine degrees Celsius for thirty minutes, followed by cooling to a lower temperature such as room temperature within three hours followed by heating and foam generation, or be subject to several high-temperature runs in succession, the foam tester 100 with forced cool-down features, for example, having the auxiliary motors 72 & 73 and associated conduits 74 & 75, and so forth, may be employed to advantage.

In FIGS. 12–14 is depicted foam tester 100 having liquid, for example, water, cooling, and in FIGS. 15 & 16 is depicted foam tester 100 having insert cooling. In general, salient features therein are present as set forth in for and in FIGS. 1–10, and certain of these features are identified numerically, for which reference to the foregoing detail is to be had. In FIGS. 12–16, cooling fluid hoses are not illustrated so as to not overburden the drawings; however, any person skilled in the art recognizes how to assemble the foam tester 100 with the same. Nonetheless, the following is noted, especially in relation to the foam tester embodiments depicted in FIGS. 12–16:

In the foam tester 100, a minimum cooling capacity of, say, one or two thousand BTUs per hour more or less is deemed to be a good value. Cooling capacities less than that may be acceptable, especially when the size and performance characteristics of the foam tester under consideration are taken into account, however.

In a bottom portion of the foam tester such as of FIGS. 1–10, as depicted in FIGS. 12–14, can be added liquid-cooling provision 90, for example, water-cooled radiators, each of which may have cooling liquid ingress 91 and exit 92. An opening may serve as ingress or exit, depending upon set up. Each radiator 90, for example, may have a 15-inch length 93, a 1.5-inch depth 94, and a 4.5-inch height 95, and be positioned with its depth 94 serving as a height and its height 95 serving as a width. Three heat exchangers may be employed, each providing a calculated cooling capacity of some 1,458 BTUs at—for the sake of calculation—at an air flow of one thousand cubic feet per minute, using tap water as cooling liquid at fifty degrees Fahrenheit, and air at seventy-three degrees Fahrenheit, assuming a linear relationship in the temperature difference and a linear air flow relationship. For example, commercially available, aluminum fin, copper tube fin-tube liquid-to-air heat exchangers such as the model 10215-S1 part 1243 (Hayden) which is also known as the model 3525K11 (McMaster-Carr Supply Co.) with 4.0-gallon-per-minute capacity, ½-inch pipe, 15-inch length by 4½-inch height by 1½-inch depth heat exchanger can be employed for water cooling even though the same are designed to accommodate oil in their cores. As an alternative, the commercially available fin-tube liguid-to-air heat exchanger model 3525K11 (McMaster-Carr Supply Co.) 5.0-gallon-per-minute capacity, ½-inch pipe, 18-inch length by 6½-inch height by 1½-inch depth heat exchanger may be employed. A suitable air blower is employed in the foam tester 100 to accommodate the cooling desiderata. When it is desired to cool the apparatus such as between test runs, the heating system is shut down; the cooling liquid is circulated, it otherwise being stopped from circulation by a tap or valve; the blowing system is, or it remains, activated, and the foam tester 100 is cooled. Such a foam tester 100 may include the following dimensions which, of course, may be considered to be approximate:

H1~25 inches H5~3 inches
H2~23 inches H6~1 inch
H3~21 inches W1~21 inches
H4~9.1 inches W2~20.9 inches as can be found illustrated in FIGS. 12–14.

In the oven volume 20 portion of the foam tester such as of FIGS. 1–10 or even of FIGS. 12–14, as depicted in FIGS. 15 & 16, can be employed insert cooling. Thus, carousel cooling insert 130 may include top 131, which need not be thermally insulating, for instance, being of a composite material, and which may in fact be greatly heat transmissive; a blower 132, for an example, the commercially available model 4C447 (Granger supply; Dayton make) electrically-powered blower, for which power may be supplied with accessory plug on top of the housing 10 or through ordinary wall plug, can provide cooling air, for example, at some one hundred thirty-five cubic feet per minute at—for the sake of calculation—0.5-inch of water, to flow initially through the top of the two center holes 133, into the oven volume 20. Preferably, radiators 90 are present, and forced air circulates thereover. The radiators 90 may be air or liquid cooled, and preferably are water cooled such as by four commercially available fin-tube liquid-to-air heat exchangers, for example, four of the aforementioned model 10215-S1 part 1243 (Hayden)/model 3525K11 3525K11 (McMaster-Carr) heat exchangers, or which may be self-cooled, for instance, containing ice or being of cold metal, and not have circulation to the outside of the foam tester 100. Returning to the drawings, insert cooling carousel 130 may also include support rod fasteners 134; handle 135; top vents 136, from which air may escape from inside the oven volume 20 to the outside, especially when the blower 132 is in operation; support rods 137, which may be of metal; bottom 138, which may be of any suitable material such as a composite; and top fluid conduit access ports 139, through which the fluid, for example, liquid water, can be transmitted into the core of the radiators 90. Cooling air may be forced from the blower 132 through the bottom of center holes 133 as well. In addition, cooling air from any auxiliary blowers in the housing of the foam tester 100 itself may be forced through the oven volume 20, venturi chamber and/or plenum, and so forth, and mix with the cooling air from the blower 132 of insert cooling carousel 130.

Although depicted as a carousel cooling insert 130, other insert(s) may be employed as an insert cooling device in the practice of the invention. For example, such another insert may be passed through a suitable openable orifice through other portion(s) of a foam tester to cool it such as through a side wall of the foam tester housing 10 and into the oven volume 20.

Figure 18:
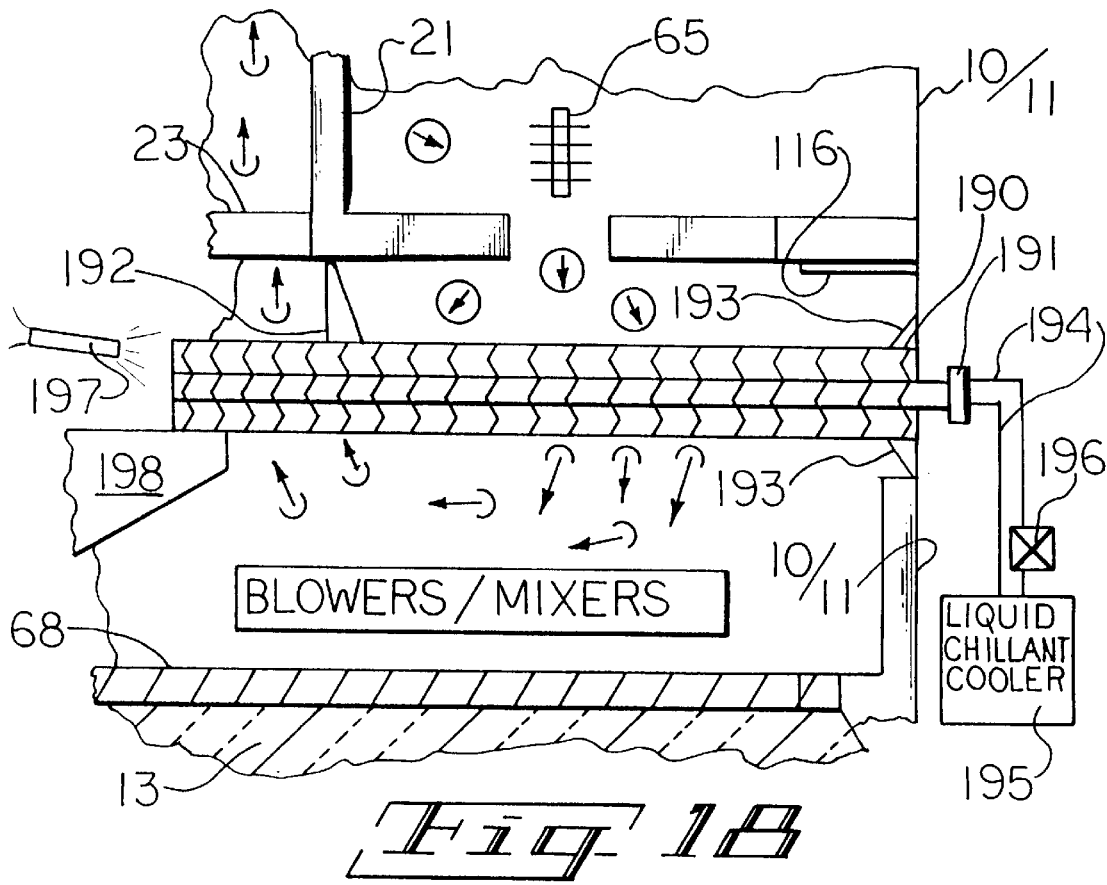
FIG. 18 is a front plan view of a portion of the foam tester of FIG. 17, taken to generally include that about circle 218 and shown in cooling mode.

In FIGS. 17 & 18 is depicted foam tester 100 having an insert drawer cooling feature, which includes, in addition to general, or in lieu of certain more specific, features of the foregoing foam tester 100 devices such as from FIGS. 1–10, 12–14 and/or 15 & 16, for example, liquid to air heat exchanger insert cooling radiator 190 having liquid connection 191; inner seal 192, for example, of a silicone containing polymer; external seals 193; cooling liquid conduits 194 for carrying liquid chillant, for example, a propylene glycol and water mixture, to and from a refrigeration device or liquid chillant cooler 195 with pressure relief device 196 present. The insert cooling radiator 190 can be removed during heating cycles of the foam tester 100 and inserted through insulated door 116, for example, along tracks or slides or other support 197 until it reaches interlock proximity switch 198 that through electrical communication will inhibit the heater 65 from running when the cooling drawer is installed by insertion, for cooling cycles. As depicted in FIG. 18, blowers and/or mixers can be located below the level of the cooling drawer insert region. The foam tester 100 can be made generally of the same or similar materials to those of the aforementioned foam testers 100 from FIGS. 1–10 & 12–16, or suitable substitutes as is the case with all the foam testers of the invention, and it may have generally similar dimensions. However, in a foam tester 100 as of FIGS. 17 & 18 following dimensions may be encountered:

H 11 Up to 28 inches.

W 11 21 inches.

The foregoing dimensions may be considered to be approximate. Standard assembly methods, suitable to the materials employed, may be conducted to make the foam tester 100.

Accordingly, cooling can be most effective and rapid.

The foam tester of the invention is a gas bath oven. Air is especially preferred as the gas owing to its standard employment in testing procedures and ubiquitousness, among other factors. Dry air is preferred as the foam-generating gas employed for bubbling in the liquid sample for testing.

CONCLUSION

The present invention is thus provided. Numerous modifications can be effected within its spirit, the literal claim scope of which is particularly pointed out as follows:

We claim:

1. A foam tester device comprising an insulated cabinet with a temperature-regulatable volume contained therein; a heater capable of heating a gas for said volume; a feature to circulate heated gas in said volume, which feature includes a plenum below said volume through which said gas can be circulated with respect to said volume by pumping said gas, and which feature further includes a perforate circulation stack mounted above said plenum and interior of said volume to a floor defining a bottom of said volume, through which gas can circulate with respect to said plenum and a portion of said volume exterior to said circulation stack; a top access system such that sample container(s), each capable of holding a liquid sample, is(are) insertable into the volume so that the same can be heated therein; and a feature to observe any sample(s) in the sample container(s) such that observation can be conducted from outside the cabinet during operation of the device, wherein provision is made therein for a sample bubbling gas to provide test foam for the liquid sample(s) in the sample container(s).

2. The device of claim 1, wherein said heated gas to be circulated is air.

3. The device of claim 2, wherein the top access system includes a top-entry sample carousel capable of holding a plurality of sample containers, and the sample container(s) is(are) insertable by inclusion with the top-entry sample carousel.

4. The device of claim 3, having an insert cooling feature.

5. A foam tester device comprising an insulated cabinet with a temperature-regulatable volume contained therein; a heater capable of beating a gas for said volume; a feature to circulate said volume through which said gas can be circulated with respect to said volume by pumping said gas, and which feature further includes a perforate circulation stack mounted above said plenum and interior of paid volume to a floor defining a bottom of said volume, through which gas can circulate with respect to said plenum and a portion of said volume exterior to said circulation stack; a top access system such that sample container(s), each capable of holding a liquid sample, is(are) insertable into the volume so that the came can be heated therein; and a feature to observe any sample(s) in the sample container(s) much that observation can be conducted from outside the cabinet during operation of the device, wherein said volume is bounded by side walls interior to inside walls of the cabinet, such that said side and inside walls provide circulation volume side channels, which contain at least one heater, and through which channels said gas can be pumped in circulation to form part of a circuit which includes flow through said circulation channel, said volume, and said plenum; and wherein at least one circulation motor provides the pumping of said gas.

6. The device of claim 5, wherein provision is made therein for a sample bubbling gas to provide test foam for the liquid sample(s) in the sample container(s).

7. A foam tester device comprising an insulated cabinet with a temperature-regulatable volume contained therein; a heater capable of beating a gas for said volume; a feature to circulate heated gas in said volume which feature includes a plenum below said volume through which said gas can be circulate with respect to said volume by pumping said gas, and which feature further includes a perforate circulation stack mounted above said plenum and interior of said volume to a floor defining a bottom of said volume, through which gap can circulate with respect to said plenum and a portion of said volume exterior to said circulation stack; a top access system such that sample container(s), each capable of holding a liquid sample, is(are) insertable into the volume so that the same can be heated therein; and a feature to observe any sample(s) in the sample container(s) such that observation can be conducted from outside the cabinet during operation of the device, which includes an insert drawer insertable through a side wall of the cabinet as a cooling feature.

8. The device of claim 7, wherein provision is made therein for a sample bubbling gas to provide test foam for the liquid sample(s) in the sample container(s).

9. The device of claim 7, wherein cooling is provided by a liquid to air heat exchanger, with the liquid in a radiator, part of the insert drawer cooling feature.

10. The device of claim 9, wherein provision is made therein for a sample bubbling gas to provide test foam for the liquid sample(s) in the sample container(s).

11. The device of claim 9, wherein the top access system includes a top-entry sample carousel capable of holding a plurality of sample containers, and the sample container(s) is(are) insertable by inclusion with the top-entry sample carousel.

12. The device of claim 11, wherein provision is made therein for a sample bubbling gas to provide test foam for the liquid sample(s) in the sample container(s).

13. A foam tester device comprising an insulated cabinet with a temperature-regulatable volume contained therein; a heater capable of heating a gas for said volume; a feature to circulate heated gas in said volume, which feature includes a plenum below said volume through which said gas can be circulated, and which feature further includes a perforate circulation stack mounted in said volume to a floor of said volume, through which gas can circulate; a top access system such that at least one sample container, each of which is capable of holding a liquid sample, is insertable into said volume so that the same can be heated therein; and a feature to observe any of the at least one sample in the at least one sample container such that observation can be conducted from outside the cabinet, wherein said access system includes a top-entry sample carousel capable of holding a plurality of sample containers, and the sample container(s) is(are) insertable by inclusion with the top-entry sample carousel; and an insert cooling feature includes a separate, top-insertable, insert cooling carousel, which is to be inserted in lieu of the top-entry sample carousel when the top-entry sample carousel is removed from said volume.

14. The device of claim 13, wherein provision is made therein for a sample bubbling gas to provide test foam for the liquid sample(s) in the sample container(s).

15. The device of claim 13, wherein cooling is provided by a liquid to air heat exchanger, with the liquid in a radiator.

16. The device of claim 15, wherein provision is made therein for a sample bubbling gas to provide test foam for the liquid sample(s) in the sample container(s).

* * * * *